United States Patent [19]

Lauderdale

[11] 4,309,502
[45] Jan. 5, 1982

[54] ENZYMATIC ASSAY FOR GLYCEROL AND TRIGLYCERIDES AND A REAGENT FOR USE THEREIN

[75] Inventor: Vivian R. Lauderdale, Encinitas, Calif.

[73] Assignee: Beckman Instruments, Inc., Fullerton, Calif.

[21] Appl. No.: 164,720

[22] Filed: Jun. 30, 1980

[51] Int. Cl.³ .......................... C12Q 1/48; C12Q 1/44
[52] U.S. Cl. ........................................ 435/15; 435/19; 435/26; 435/198; 435/810; 435/884
[58] Field of Search ................... 435/4, 11, 15, 19, 26, 435/198, 810, 884

[56] References Cited

U.S. PATENT DOCUMENTS

| | | | |
|---|---|---|---|
| 3,513,073 | 5/1970 | Mauvernay et al. | 435/198 |
| 3,703,591 | 11/1972 | Bucolo et al. | 435/15 |
| 3,759,793 | 9/1973 | Stork et al. | 435/15 |
| 3,862,009 | 1/1975 | Wahlefeld et al. | 435/15 |
| 3,898,130 | 8/1975 | Komatsu | 435/19 |
| 4,001,089 | 1/1977 | Stavropoulos et al. | 23/230 B |
| 4,011,045 | 3/1977 | Bonderman | 23/230 B |
| 4,038,146 | 7/1977 | Nonaka et al. | 435/15 |
| 4,045,297 | 8/1977 | Weeks et al. | 435/15 |
| 4,056,442 | 11/1977 | Huang et al. | 435/198 |
| 4,066,508 | 1/1978 | Rauschee et al. | 435/15 |

FOREIGN PATENT DOCUMENTS

| | | |
|---|---|---|
| 2065556 | 4/1974 | Fed. Rep. of Germany . |
| 2000127 | 12/1974 | Fed. Rep. of Germany . |
| 1441642 | 7/1976 | United Kingdom ................. 435/15 |

OTHER PUBLICATIONS

Frederickson et al., New Eng. J. Med., 276:34, 1967.
Eggstein et al., Kln. Wschr., 44:262,267, 1966.
Bucolo et al., Clin. Chem., 19:476, 1963.
Wahlefeld, Methods of Enzymatic Analysis, H. U. Bergmeyer, ed. p. 1831, Academic Press, N.Y., 1974.
Pinter et al., Arch. Biochem. Biophys., 121:404 1966.

Primary Examiner—Peter A. Hruskoci
Attorney, Agent, or Firm—R. J. Steinmeyer; J. E. Vanderburgh; Robert S. Frieman

[57] ABSTRACT

An assay which is capable of determining the endogenous glycerol and endogenous triglycerides content of a sample without the necessity of performing a separate glycerol assay. The assay of the instant invention can be performed in a single cuvette and is made possible by the use of a novel reagent kit.

The reagent kit is of the type comprising lipase; glycerol kinase; adenosine triphosphate; and at least one reagent capable of being used to assay glycerol-1-phosphate or adenosine diphosphate. This reagent kit is characterized in that the lipase employed therein is from Staphylococcus epidermidis NRRL B-12072. In the absence of an auxiliary agent, this lipase does not cleave triglycerides to glycerol. Accordingly, the reagent kit further comprises, as the auxiliary agent, a surfactant which is capable of activating the lipase. Because these surfactants do not absorb at either 340 or 520 nm, one can determine a sample's endogenous glycerol content and endogenous triglycerides content in a single cuvette.

19 Claims, 4 Drawing Figures

PRIOR ART ULTRA VIOLET (UV; 340 nm) METHODOLOGY:

LIPASE AND REAGENTS OTHER THAN GLYCEROL KINASE $\longrightarrow$ BLANK READING $\xrightarrow[\text{ADDITION}]{\text{SERUM}}$ $OD^2$ DUE TO ADDITION OF SERUM $\xrightarrow[\text{KINASE ADDITION}]{\text{GLYCEROL}}$ $\Delta OD_{uv}$ DUE TO ENDOGENOUS GLYCEROL AND ENDOGENOUS TRIGLYCERIDE

PRIOR ART COLORIMETRIC (C; 520 nm) METHODOLOGY:

LIPASE AND ALL OTHER REAGENTS $\longrightarrow$ BLANK READING $\xrightarrow[\text{ADDITION}]{\text{SERUM}}$ $\Delta OD_c$ DUE TO ENDOGENOUS GLYCEROL AND ENDOGENOUS TRIGLYCERIDE 1. nm DENOTES NANOMETERS
2. $\Delta$ OD DENOTES CHANGE IN OPTICAL DENSITY

FIG 1

ULTRA VIOLET (340nm) METHODOLOGY — WITHIN SCOPE OF INVENTION

LIPASE FROM STAPHYLOCOCCUS EPIDERMIDIS NRRL B-12072 AND REAGENTS OTHER THAN GLYCEROL KINASE → BLANK READING —SERUM ADDITION→ Δ OD DUE TO ADDITION OF SERUM

ADDITION OF SURFACANT CAPABLE OF ACTIVATING LIPASE FROM STAPHYLOCOCCUS EPIDERMIDIS NRRL B-12072 → Δ OD DUE TO ENDOGENOUS TRIGLYCERIDE

—GLYCEROL KINASE ADDITION→ Δ OD DUE TO ENDOGENOUS GLYCEROL

COLORIMETRIC (520nm) METHODOLOGY — WITHIN SCOPE OF INVENTION

LIPASE FROM STAPHYLOCOCCUS EPIDERMIDIS NRRL B-12072 AND ALL OTHER REAGENTS → BLANK READING —SERUM ADDITION→ Δ OD DUE TO ENDOGENOUS GLYCEROL

ADDITION OF SURFACANT CAPABLE OF ACTIVATING LIPASE FROM STAPHYLOCOCCUS EPIDERMIDIS NRRL B-12072 → Δ OD DUE TO ENDOGENOUS TRIGLYCERIDE

FIG 2

ENZYMATIC ASSAY FOR GLYCEROL AND TRIGLYCERIDES AND A REAGENT FOR USE THEREIN

BACKGROUND OF THE INVENTION

1. Field of the Invention

This invention relates to an enzymatic analysis of endogenous glycerol and triglycerides in a sample to be assayed.

2. Description of the Prior Art

The measurement of serum triglycerides is important in the diagnosis of hyperlipoproteinemia and in the prediction, detection, and monitoring of atherosclerosis (1).

In the prior art, triglycerides are generally determined by a combination of hydrolysis to glycerol and free fatty acids and measurement of the amount of glycerol released. The most commonly used prior art methods involve alkaline hydrolysis and either chemical or enzymatic measurement of glycerol. Chemical means of analysis generally rely on measurement of the product of periodate oxidation of glycerol. Eggstein et al. (2) developed an enzymatic method for measuring glycerol released from triglycerides by alkaline hydrolysis. This method was based on the coupled reaction sequence catalyzed by glycerol kinase, pyruvate kinase, and lactate dehydrogenase. A method for complete enzymatic hydrolysis of triglycerides avoiding the need for serum pretreatment was described by Bucolo et al. (3) using a combination of lipase and at least one proteolytic enzyme. Wahlefeld (4) reported that certain esterases could be combined with a lipase to achieve complete hydrolysis of triglycerides. Both methods employed a coupled enzymatic reaction sequence (5) to measure glycerol.

Although there has been extensive research in the area of triglyceride analysis (6–16), none of the triglyceride analyses reported to date are capable of differentiating between the endogenous glycerol and endogenous triglyceride content of a sample without the necessity of having to perform a separate glycerol analysis on the sample being assayed. Instead, all of these prior art analyses include in their reported triglyceride content the amount of endogeneous triglyceride as well as the amount of endogeneous glycerol present in the sample being assayed. The reason for this can be seen from the schematic procedures set forth in FIG. 1. As shown in both of the schematic procedures of FIG. 1, the $\Delta$ $OD_{uv}$ and $\Delta$ $OD_c$ include a contribution from the assayed sample's endogenous glycerol content as well as the assayed sample's endogenous triglyceride content. In neither the ultraviolet nor colorimetric methods is it possible to add the lipase to the reaction mixture after obtaining a $\Delta$ OD due solely to the sample's endogenous glycerol content. This is because lipase absorbs at both 340 nm and 520 nm and therefore would introduce an error into the resulting $\Delta$ OD measurement. Therefore, in the prior art, if one desired to know the endogeneous triglyceride content of a sample, one would have to perform a separate glycerol analysis on the sample being assayed. The endogenous glycerol content found via this separate assay would then have to be subtracted from the data obtained using the prior art triglyceride analysis to yield the amount of endogenous triglyceride present in the sample.

It would be very desirable to have an assay which would be capable of determining the endogenous glycerol and endogenous triglycerides content of a sample without the necessity of performing a separate glycerol assay. Such a simplified procedure would entail the use of a single cuvette as opposed to the prior art necessity of employing at least 2 cuvettes. This simplified procedure would require less reagents as well as a smaller sample size than required to perform the two prior art assays. In addition, the simplified procedure could be readily automated, thereby effecting a major increase in productivity.

References

1. Frederickson et al., *New Eng. J. Med.*, 276:34 (1967).
2. Eggstein et al., *Klin. Wschr.*, 44:262,267 (1966).
3. Bucolo et al., *Clin. Chem.*, 19:476 (1973).
4. Wahlefeld, *Methods of Enzymatic Analysis*, (H. U. Bergmeyer, ed) pp. 1831, Academic Press, New York (1974).
5. Pinter et al., *Arch. Biochem. Biophys.*, 121:404 (1966).
6. U.S. Pat. No. 3,513,073
7. U.S. Pat. No. 3,703,591
8. U.S. Pat. No. 3,862,009
9. U.S. Pat. No. 3,898,130
10. U.S. Pat. No. 4,001,089
11. U.S. Pat. No. 4,011,045
12. U.S. Pat. No. 4,038,146
13. U.S. Pat. No. 4,045,297
14. U.S. Pat. No. 4,056,442
15. U.S. Pat. No. 4,066,508
16. German Pat. No. 2,065,556

SUMMARY OF THE INVENTION

In accordance with the present invention there is provided an assay which is capable of determining the endogeneous glycerol and endogeneous triglycerides content of a sample without the necessity of performing a separate glycerol assay. The assay of the instant invention can be performed in a single cuvette and is made possible by the use of a novel reagent kit.

The reagent kit of the instant invention is of the type comprising lipase; glycerol kinase; adenosine triphosphate; and at least one reagent capable of being used to assay glycerol-1-phosphate or adenosine diphosphate. This reagent kit is characterized in that the lipase employed therein is from *Staphylococcus epidermidis* NRRL B-12072. Without the presence of an auxiliary agent, the lipase from *Staphylococcus epidermidis* NRRL B-12072 does not cleave triglyceride to glycerol. Accordingly, the reagent kit of the instant invention further comprises, as the auxiliary agent, a surfactant which is capable of activating the lipase from *Staphylococcus epidermidis* NRRL B-12072. Because these surfactants do not absorb at either 340 or 520 nm, one, employing the reagent kit of the instant invention, can now determine a sample's endogeneous glycerol content and endogeneous triglyceride content by employing any one of the numerous assay methodologies within the scope of this invention without the necessity of performing a separate glycerol assay. Examples of these methodologies include, but are not limited to, those represented by the schematic procedures set forth in FIG. 2. It should be noted that the lipase from *Staphylococcus epidermidis* NRRL B-12072 need not necessarily be added at the times shown in FIG. 2 but can be added at any time prior to the addition of the appropriate surfactant to the reaction mixture. If the lipase is added to the reaction mixture at some time subsequent to that shown in FIG. 2, one would, of course, have to make an additional ΔOD reading in order to subtract from the next ΔOD measurement the ΔOD caused by such lipase addition.

Still other features and attendant advantages of the present invention will become apparent to those skilled in the art from a reading of the following detailed description of the preferred embodiments.

BRIEF DESCRIPTION OF THE DRAWINGS

FIG. 1 is a schematic representation of a prior art ultraviolet methodology and a prior art colorimetric methodology.

FIG. 2 is a schematic representation of an ultraviolet methodology within the scope of this invention and a colorimetric methodology within the scope of this invention.

DESCRIPTION OF THE PREFERRED EMBODIMENT

Figure 3:
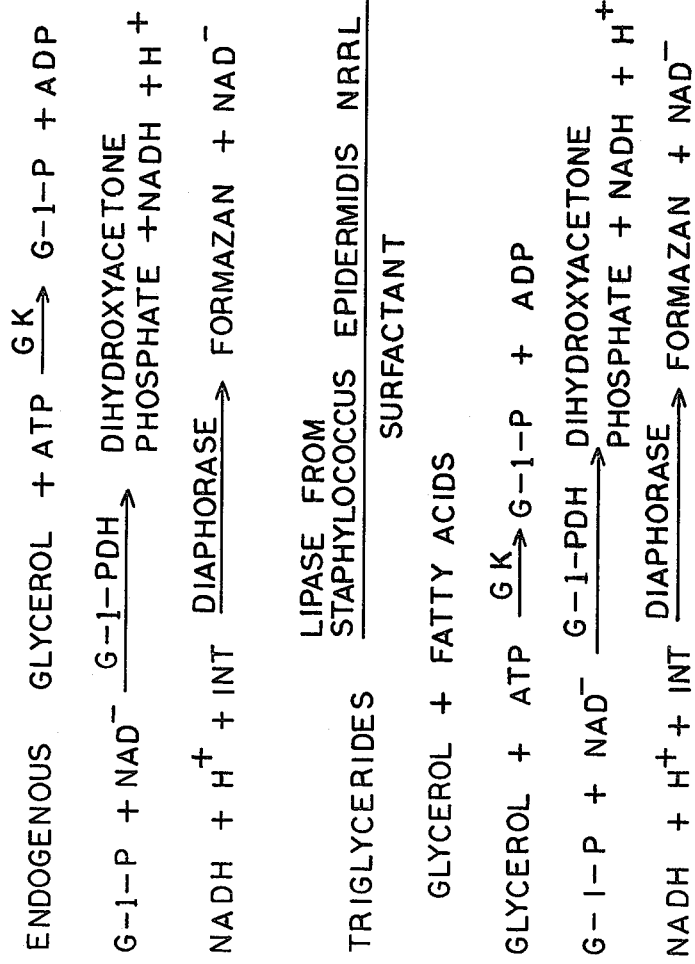
FIG. 3 depicts one of the colorimetric enzymatic reaction sequences capable of being employed in the assay of the instant invention.

Surfactants which are capable of activating a lipase from Staphylococcus epidermidis NRRL B-12072 include, but are not limited to, aliphatic esters of sulfosuccinic acid, octylphenoxy polyethoxyethanol, polyethoxylated tall oils, ethoxylated alcohol, and mixtures thereof. Preferably, octylphenoxy polyethoxyethanol is in the p-t-octylphenoxy polyethoxyethanol configuration. The aliphatic esters of sulfosuccinic acid also preferably have an alkyl moiety containing 4 to 16 carbon atoms. Examples of aliphatic esters of sulfosuccinic include, but are not limited to, sodium dihexyl sulfosuccinate, sodium dicyclohexyl sulfosuccinate, sodium diamyl sulfosuccinate, sodium diisobutyl sulfosuccinate, and mixtures thereof.

The tall oils are preferably ethoxylated with from about 5 to about 25, and more preferably from about 10 to 20, moles of ethylene oxide.

Optimally, the surfactant employed in the specific ultraviolet methodology of the instant invention schematically illustrated in FIG. 2 is a mixture of 0.075% sodium dihexyl sulfosuccinate and 0.075% octylphenoxy polyethoxyethanol.

Optimally, the surfactant employed in the specific colorimetric methodology of the instant invention schematically illustrated in FIG. 2 is a mixture of 0.01% of a tall oil ethoxylated with 16 moles of ethylene oxide and 0.01% ethoxylated alcohol.

The lipase employed in the instant invention is derived from a microorganism having the following description:

(a) Spheres, approximately 0.7 μm in diameter after growth for 24 hours in Difco Brain Heart Infusion. Cells are usually found as irregular clusters, but occasionally pairs or short chains of 4–8 cells can be observed.

(b) Colonies after growth for 24 hours of Difco Brain Heart Infusion agar plates are as follows: Circular, approximately 1–2 mm in diameter, convex with a smooth surface, entire edges. White colonies.

(c) Fermentative metabolism in O–F medium; acid from glucose in presence and absence of air.

(d) Acid produced from mannitol in presence of air; no air from mannitol in absence of air.

(e) Coagulase positive.

(f) Catalase positive.

(g) Sensitive to following antibiotics when performed by Kerby-Bauer procedure: chloramphenicol, erythromycin, kanamycin, neomycin, novobiocin, penicillin, stretomycin, tetracyline.

This description is compatible with the description for Staphylococcus epidermidis according to the 8th edition of Bergey's Manual of Determinative Bacteriology (1974). A subculture of this living organism can be obtained upon request from the permanent collection of the Northern Regional Research Center, 1815 North University Street, Peoria, Ill., U.S. 61604. Its accession number in this repository is NRRL B-12072.

The lipase can be removed from Staphylococcus epidermidis NRRL B-12072 via techniques well known to those skilled in the art. See Dixon et al., Enzymes, New York Academic Press, N.Y., N.Y. (1964) and Gutcho, Microbial Enzyme Production: Chemical Technology Review #28, Noyes Data Corp., Park Ridge, N.J. (1974), said publications being incorporated herein in toto by reference.

A typical procedure which can be employed to optimally grow Staphylococcus epidermidis NRRL B-12072 and to isolate the extracellularly produced lipase therefrom is as follows:

Staphylococcus epidermidis NRRL B-12072 bacteria is fermented with mild stirring and oxygenation in a fermentation medium comprising 2.5% autolyzed yeast extract, 0.05% KCl, 0.5% N-Z-AMINE A brand nutrient sold by Staley Corp., 0.5% Hy-Soy brand soy protein hydrolysate powder sold by Sheffield Corp., 0.5% $(NH_4)_2SO_4$, 1.3% $K_2HPO_4$, and 0.05% $MgSO_4$. This fermentation procedure can be conducted for any convenient period of time, e.g., 12 to 36, preferably 16 to 24, hours.

After completion of the fermentation procedure, a flocculating agent, e.g., C7 Primafloc brand flocculating agent sold by Rohm and Haas, is added to the fermentation broth. The resulting solution is then passed through a desludger and the solid constituents are removed therefrom. The residual turbidity present in the slightly turbid solution is removed via filtration through diatomeous earth.

The clear filtrate can be concentrated by any technique known to those skilled in the art, e.g., via the use of a suitable molecular sieve.

The concentrated solution is then contacted with a sufficient amount (approximately 35%) of ammonium sulfate to precipitate non-essential proteins therefrom. Lipase is precipitated out of the resulting solution by contacting the resulting solution with about 85% ammonium sulfate.

Next, the precipitated lipase is reconstituted and dialyzed to remove any ammonium sulfate present therein. A purified lipase is obtained by passing the reconstituted lipase through a Whatman DE 52 brand microgranular anion exchange column containing diethylaminoethyl cellulose. When necessary to remove occasional residual contamination, this purified lipase can be further treated with protamine sulfate and/or heat treatment via techniques well known to those skilled in the art.

In general, the reagent kit of the instant invention can comprise (a) a lipase from *Staphylococcus epidermidis* NRRL B-12072; (b) glycerol kinase; (c) adenosine triphosphate; (d) at least one reagent capable of being used to assay glycerol-1-phosphate or adenosine diphosphate; and (e) a surfactant capable of activating the lipase from *Staphylococcus epidermidis* NRRL B-12072. Reagents a–d can be in any preselected distribution in one or more vials but the surfactant (e) must be present in a separate vial.

When the reagent kit of the instant invention is to be used in an ultraviolet (340 nm) methodology, ingredients a, c, and d can be in a first vial; glycerol kinase can be in a second vial; and the surfactant can be in a third vial.

For use in a colorimetric (520 nm) methodology, the reagent kit can be formulated so that ingredients a–d are in a first vial and the surfactant is in a second vial.

The lipase from *Staphylococcus epidermidis* NRRL B-12072 can be employed to perform the enzymatic hydrolysis of triglycerides in any of the coupled enzymatic reaction sequences known to those skilled in the art. Examples of such triglyceride assay systems are set forth in U.S. Pat. No. 3,703,591 (7); U.S. Pat. No. 4,001,089 (10); U.S. Pat. No. 4,038,146 (12); U.S. Pat. No. 4,045,297 (13); and U.S. Pat. No. 4,056,442 (14), said publications being incorporated herein in toto by reference. More particularly, one of the colorimetric (520 nm) enzymatic reaction sequences capable of being employed in the assay of the instant invention is shown in FIG. 3, wherein (1) endogenous glycerol is reacted with adenosine triphosphate (ATP) in the presence of glycerol kinase (GK) to form glycerol-1-phosphate (G-1-P) and adenosine diphosphate (ADP);

(2) G-1-P is reacted with a co-enzyme selected from a group consisting of β-nicotamide-adenine-dinucleotide (NAD), β-nicotimide-adenine-dinucleotide phosphate (NADP), and mixtures thereof in the presence of glycerol phosphate dehydrogenase (G-1-PDH) to form dihydroxyacetone phosphate and the reduced form of the co-enzyme;

(3) the reduced form of the co-enzyme is reacted with 2-(p-indophenyl)-3-p-nitrophenyl-5-phenyl-tetrazolium chloride (INT) in the presence of diaphorase to form formazan and the co-enzyme; and (4) the formation of the formazan formed in step (3) is spectrophotometrically measured.

After measuring the formation of formazan, a surfactant capable of activating a lipase from *Staphylococcus epidermidis* NRRL B-12072 is then added to the reaction mixture which already has present therein the lipase from *Staphylococcus epidermidis* NRRL B-12072. In the presence of the activated lipase, the triglycerides are then transformed to glycerol and fatty acids. The glycerol is then reacted with ATP in the presence of GK to form G-1-P and ADP and coupled reaction steps (2) and (3) are performed. The formation of formazan is again spectrophotometrically measured to determine the amount of endogenous triglycerides present in the sample being assayed.

Figure 4:
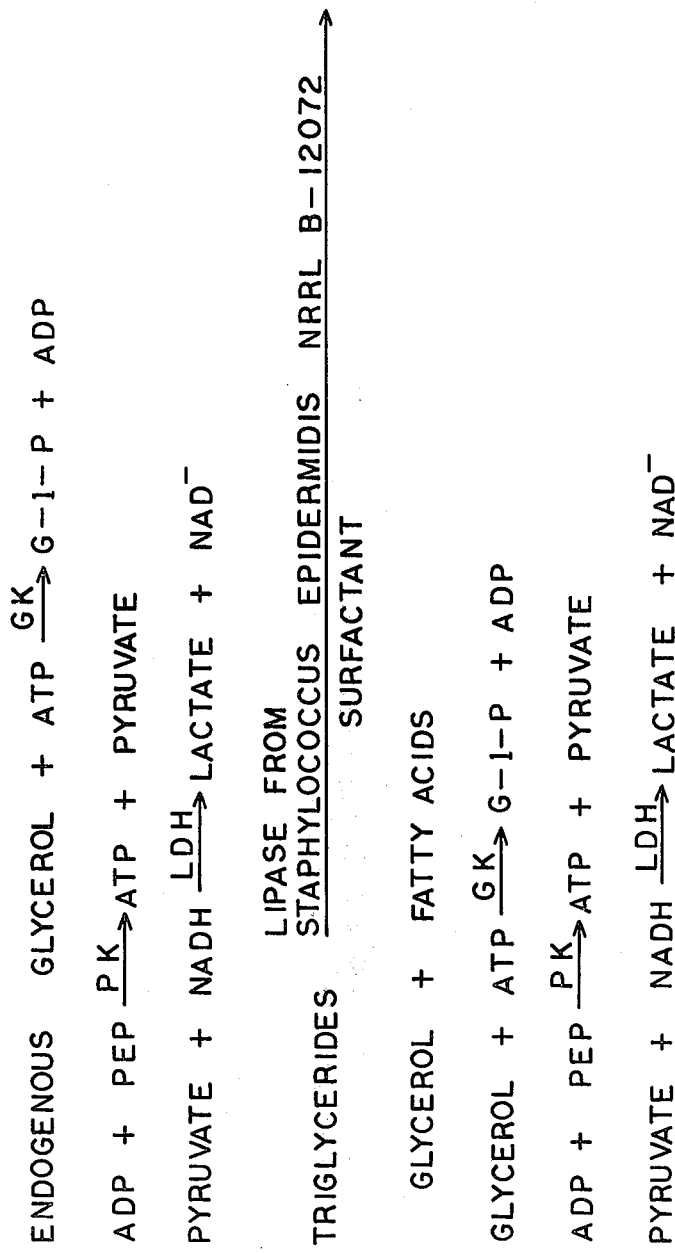
FIG. 4 depicts one of the ultraviolet enzymatic reaction sequences that can be employed in the instant invention.

An example of one of the ultraviolet (340 nm) enzymatic reaction sequences that can be employed in the instant invention is shown in FIG. 4, wherein (1) endogenous glycerol is reacted with ATP in the presence of GK to form G-1-P and ADP;

(2) ADP is reacted with phosphoenol pyruvate (PEP) in the presence of pyruvate kinase (PK) to form ATP and pyruvate;

(3) pyruvate is reacted with a reduced co-enzyme in the presence of lactate dehydrogenase (LDH) to form lactate and the oxidized form of the co-enzyme;

(4) the formation of the oxidized co-enzyme is measured.

After measuring the formation of oxidized co-enzyme, a surfactant capable of activating a lipase from *Staphylococcus epidermidis* NRRL B-12072 is then added to the reaction mixture which already has present therein the lipase from *Staphylococcus epidermidis* NRRL B-12072. The activated lipase then transforms the triglycerides to glycerol and fatty acids. The glycerol is reacted with ATP in the presence of GK to form G-1-P and ADP and the coupled reaction steps (2) and (3) are performed. The formation of the oxidized co-enzyme is again measured to determine the amount of endogeneous triglycerides in the sample being assayed.

The exact concentrations of the various constituents of the triglyceride kit employed in any particular assay sequence of the instant invention is not critical provided that the ingredients are present in an amount such that the endogenous glycerol and endogenous triglyceride to be assayed are the limiting components of the reaction sequence.

With respect to the above colorimetric coupled reaction sequence, a kit suitable for use therein can comprise at least about 25, preferably from about 25 to about 150, and more preferably from about 50 to about 100 International Units per liter (IU/l) of the lipase from *Staphylococcus epidermidis* NRRL B-12072; at least about 300, preferably from about 300 to about 1,500, and more preferably about 600 to about 1,200 IU/l of glycerol kinase; at least about 0.5, preferably from about 0.5 to about 3, and more preferably from about 1 to about 2 mM ATP; at least about 0.2, preferably from about 0.2 to about 2, and more preferably from about 0.5 to about 1 mM of a co-enzyme selected from a group consisting of NAD, NADP, derivatives thereof, and mixtures thereof; a least about 2, preferably from about 2 to about 30, and more preferably from about 10 to about 20 mM $Mg^{++}$; at least about 4,000, preferably from about 4,000 to about 25,000, and more preferably from about 10,000 to about 25,000 IU/l of G-1-PDH; at least about 2,000, preferably from about 2,000 to about 20,000, and more preferably from about 5,000 to about 15,000 IU/l of diaphorase; and at least about 0.1, preferably from about 0.1 to about 0.25, and more preferably from about 0.12 to about 0.2 g/l of INT.

With respect to the above ultraviolet coupled reactions, a reagent kit suitable for use therein can comprise at least about 20, preferably from about 20 to about 150, and more preferably from about 50 to about 100 IU/l of the lipase from *Staphylococcus epidermidis* NRRL B-12072; at least about 100, preferably from about 1,000 to about 2,500, and more preferably from about 2,000 to about 3,000 IU/l GK; at least about 0.1, more preferably from about 0.1 to about 0.8, and more preferably from about 0.3 to about 0.8 mM ATP; at least about 0.2, preferably from about 0.2 to about 0.6, and more preferably from about 0.25 to about 0.35 mM of the reduced co-enzyme selected from a group consisting of NADH, NADPH, derivatives thereof and mixtures thereof; at least about 1, preferably from about 1 to about 10, and more preferably from about 3 to about 8 mM $Mg^{++}$; at least about 0.1, preferably from about 0.1 to about 0.8, and more preferably from about 0.2 to about 0.6 mM PEP; at least about 300, preferably from about 300 to about 6,000, and more preferably from about 2,500 to about 3,500 IU/l PK; and at least about 300, preferably from about 300 to about 2,000, and more preferably from about 1,000 to about 1,800 IU/l LDH.

Any buffer having a suitable pH range and which is compatible with the other constituents of the reagent kit can be employed in this invention. Such buffers include, but are not limited to, phosphate, piperazine-N,N'-bis(2-ethanesulfonic acid) (PIPES), N-2-hydroxyethylpiperazine-N'-2-ethanesulfonic acid (HEPES), N-tris-(hydroxymethyl)methyl-2-amino-ethanesulfonic acid (TES), N,N-bis-(2-hydroxyethyl)-2-aminoethanesulfonic acid (BES), and triethanolamine hydrochloride (TEA) buffers. Although the concentration of buffer is not critical, it is preferable that the buffer be present in an amount of at least about 0.01, more preferably in an amount from about 0.01 to about 0.5, molar (M).

A phosphate buffer is preferred for use in the ultraviolet enzymatic reaction sequence set forth above and a TEA buffer is preferred for use in the colorimetric enzymatic reaction sequence set forth above.

The pH of the buffer employed in the above colorimetric kit can be from about 6 to about 9 and preferably from about 7 to about 8.

The pH of the buffer employed in the above ultraviolet kit can be from about 6 to about 8 and preferably from about 6.5 to about 7.5.

The following examples are provided for the purpose of further illustration only and are not intended to be limitations on the disclosed invention.

EXAMPLE 1

The following is the composition and distribution of a preferred reagent within the scope of the present invention for use in a colorimetric enzymatic reaction sequence:

| Ingredients | Concentration in Vial as Formulated |
|---|---|
| First Vial | |
| Lipase from *Staphylococcus epidermidis* NRRL B-12072 | 75 IU/l |
| GK | 920 IU/l |
| ATP | 1.3 mM |
| Co-enzyme | 0.68 mM |
| Mg$^{++}$ | 16.78 mM |
| G-1-PDH | 15,000 IU/l |
| Diaphorase | 10,000 IU/l |
| INT | 0.187 g/l |
| Second Vial | |
| Tall oil ethoxylated with 16 moles of ethylene oxide | 1% aqueous |
| Ethoxylated alcohol | 1% aqueous |

The reagent is prepared in 0.05 M TEA buffer, pH 7.5±0.1.

With respect to the specific colorimetric methodology of the instant invention schematically illustrated in FIG. 2, the surfactant optimally employed therein is a mixture of 1% of a tall oil ethoxylated with 16 moles of ethylene oxide and 1% ethoxylated alcohol.

EXAMPLE 2

The following is the composition and distribution of a preferred reagent within the scope of the present invention for use in an ultraviolet enzymatic reaction sequence:

| Ingredients | Concentration in Vial as Formulated |
|---|---|
| First Vial | |
| Lipase from *Staphylococcus epidermidis* NRRL B-12072 | 50 IU/l |
| ATP | 0.3 mM |
| Reduced co-enzyme | 0.3 mM |
| Mg$^{++}$ | 5 mM |
| PEP | 0.37 mM |
| PK | 2,900 IU/l |
| LDH | 1,485 IU/l |
| Second Vial | |
| GK | 250 IU/ml |
| Third Vial | |
| Sodium dihexylsulfosuccinate | 7.5% aqueous |
| Octylphenoxy polyethoxyethanol | 7.5% aqueous |

The reagent is prepared in 0.05 M phosphate buffer pH 7.1±0.1.

EXAMPLE 3

Single Cuvette Assay Within Scope of Invention

1. An aliquot (1 ml) of the first vial of Example 2 was placed in a cuvette together with a 10 μl aliquot of the second vial of Example 2. The cuvette and its contents were incubated for about 5 minutes in a spectrophotometer which was set at 340 nm and 37° C. After completion of the incubation period, a spectrophotometer reading was made of the cuvette and its contents to yield a first optical density reading (OD$_1$).

2. A sample (10 μl) of water was added to the cuvette's contents and the cuvette and its contents were shaken. After shaking, the cuvette and its contents were incubated for about 5 minutes in the spectrophotometer. At the end of this incubation period, a spectrophotometric reading was again made of the cuvette and its contents to yield a second optical density reading (OD$_2$).

3. Into the cuvette was now placed a 10 μl aliquot of the third vial of Example 2 and the cuvette and its contents were shaken. After shaking, the cuvette and its contents were incubated for about 10 minutes in the spectrophotometer. At the end of this incubation period, a spectrophotometric reading was again made of the cuvette and its contents to yield a third optical density reading (OD$_3$).

Steps 1 through 3 were then repeated for each of the eight serum samples assayed with the sole modification being the use of a 10 μl serum sample in step 2 in place of the 10 μl water sample employed therein.

The following formula was used to calculate the endogenous glycerol content of the serum sample assayed:

$$\frac{(OD_2 - OD_1 \text{ sample})}{6.22 \times 10 \times S_v} -$$
$$(OD_2 - OD_1 \text{ water}) \times T_{v2} \times 92 = \text{mg\% endogenous glycerol}$$

wherein OD$_1$ and OD$_2$ have been defined above; 6.22 is the extinction coefficient of NADH at 340 nm; 92 is the molecular weight of glycerol; T$_{v2}$ is the total volume present in the cuvette at the time of the OD$_2$ reading; and S$_v$ is the sample volume. The data obtained from the above calculations is set forth in Table I.

The following formula was used to calculate endogenous triglyceride content of the sample assayed:

$$\frac{(OD_3 - OD_2) \times T_{v3} \times 885}{6.22 \times 10} = \text{mg\% endogenous triglycerides}$$

wherein $OD_3$, $OD_2$ and 6.22 are as defined above; $T_{v3}$ is the total volume present in the cuvette at the time of the $OD_3$ reading; and 885 is the molecular weight of triglycerides. The data obtained from the above calculations is also set forth in Table I.

EXAMPLE 4

Prior Art Alcohol Saponification Procedure for Combined Endogenous Glycerol and Endogenous Triglycerides Serum samples were assayed for their combined endogenous glycerol and endogenous triglycerides content by a prior art alcohol saponification procedure as set forth in Bucolo et al. (3). The data obtained therefrom is set forth in Table I.

EXAMPLE 5

Prior Art Ultraviolet Procedure for Combined Endogenous Glycerol and Endogenous Triglycerides Serum samples were assayed for their combined endogenous glycerol and endogenous triglycerides content by a prior art ultraviolet procedure as set forth in Beckman Instructions 015-555483-A, Beckman Instruments, Inc., Fullerton, CA 92634. The data obtained therefrom is set forth in Table I.

EXAMPLE 6

Prior Art Procedure for Endogenous Glycerol

Serum samples were assayed for their endogenous glycerol content by a prior art free glycerol in serum procedure as set forth in Bucolo et al. (3). The data obtained therefrom is set forth in Table I.

those skilled in the art. These are intended to be comprehended as within the scope of this invention.

The embodiments of the invention in which an exclusive property or privilege is claimed are defined as follows:

1. A kit for use in analysis of endogenous glycerol and triglycerides in a sample to be assayed comprising in association:
    (a) a lipase from *Staphylococcus epidermidis* NRRL B-12072;
    (b) glycerol kinase;
    (c) adenosine triphosphate;
    (d) at least one reagent capable of being used to assay glycerol-1-phosphate or adenosine diphosphate formed in the glycerol kinase reaction, wherein said reagent, adenosine triphosphate, glycerol kinase and said lipase from *Staphylococcus epidermidis* NRRL B-12072 are present in any preselected distribution in one or more vials; and
    (e) a surfactant, present in a separate vial, capable of activating said lipase from *Staphylococcus epidermidis* NRRL B-12072.

2. The kit of claim 1 wherein said surfactant is selected from a group consisting of polyethoxylated tall oils, aliphatic esters of sulfosuccinic acid, octylphenoxy polyethyoxyethanol, and mixtures thereof.

3. The kit of claim 1 wherein said surfactant is selected from a group consisting of aliphatic esters of sulfosuccinic acid, p-t-octylphenoxy polyethoxyethanol, and mixtures thereof.

4. The kit of claim 3 wherein said aliphatic esters of sulfosuccinic acid have an alkyl moiety containing from 4 to 16 carbon atoms.

5. The kit of claim 4 wherein said aliphatic esters of sulfosuccinic acid are selected from a group consisting of sodium dihexyl sulfosuccinate, sodium dicyclohexyl sulfosuccinate, sodium diamyl sulfosuccinate, sodium diisobutyl sulfosuccinate, and mixtures thereof.

6. The kit of claim 5 wherein said aliphatic ester of

TABLE I

| Procedure | Serum Sample | | | | | | | | | | | |
|---|---|---|---|---|---|---|---|---|---|---|---|---|
| | 1 | | | 2 | | | 3 | | | 4 | | |
| | G[1] | T[2] | G+T[3] | G | T | G+T | G | T | G+T | G | T | G+T |
| | Within Scope of Invention | | | | | | | | | | | |
| Example 3 | 87 | 532 | 619 | 58 | 562 | 620 | 36 | 325 | 361 | 44 | 362 | 406 |
| | Prior Art | | | | | | | | | | | |
| Example 4 | — | — | 620 | — | — | 673 | — | — | 315 | — | — | 365 |
| Example 5 | — | — | 557 | — | — | 487 | — | — | 335 | — | — | 370 |
| Example 6 | 67 | — | — | 58 | — | — | 44 | — | — | 44 | — | — |

[1] G denotes endogenous glycerol
[2] T denotes endogenous triglycerides
[3] G + T denotes combined endogenous glycerol and endogenous triglycerides

| Procedure | Serum Sample | | | | | | | | | | | |
|---|---|---|---|---|---|---|---|---|---|---|---|---|
| | 5 | | | 6 | | | 7 | | | 8 | | |
| | G | T | G+T | G | T | G+T | G | T | G+T | G | T | G+T |
| | Within Scope of Invention | | | | | | | | | | | |
| Example 3 | 44 | 335 | 399 | 44 | 318 | 362 | 51 | 481 | 532 | 36 | 318 | 354 |
| | Prior Art | | | | | | | | | | | |
| Example 4 | — | — | 347 | — | — | 323 | — | — | 511 | — | — | 369 |
| Example 5 | — | — | 379 | — | — | 335 | — | — | 505 | — | — | 357 |
| Example 6 | 47 | — | — | 37 | — | — | 55 | — | — | 35 | — | — |

Table I demonstrates that the data obtained via the single cuvette assay of the instant invention is comparable to the data obtained via the more laborious prior art techniques.

Based on this disclosure, many other modifications and ramifications will naturally suggest themselves to sulfosuccinic acid is sodium dihexyl sulfosuccinate.

7. The kit of claims 1-5 or 6 wherein said reagent is capable of being used to assay glycerol-1-phosphate and comprises a co-enzyme selected from a group consisting of NAD, NADP, derivatives thereof, and mixtures thereof; glycerol phosphate dehydrogenase; diaphorase; and 2-(p-indophenyl)-3-p-nitrophenyl-5-phenyl-tetrazolium chloride.

8. The kit of claims 1–5 or 6 having a pH of from about 6 to about 9 and comprising:
   (a) at least about 25 IU/l of said lipase from *Staphylococcus epidermidis* NRRL B-12072;
   (b) at least about 300 IU/l glycerol kinase;
   (c) at least about 0.5 mM adenosine triphosphate;
   (d) at least about 0.2 mM of a co-enzyme selected from a group consisting of NAD, NADP, derivatives thereof, and mixtures thereof;
   (e) at least about 2 mM $Mg^{++}$;
   (f) at least about 4,000 IU/l glycerol phosphate dehydrogenase;
   (g) at least about 2,000 IU/l diaphorase; and
   (h) at least about 0.1 g/l 2-(indophenyl)-3-p-nitrophenyl-5-phenyl-tetrazolium chloride.

9. The kit of claims 1–5 or 6 having a pH of from about 6 to about 9 and comprising:
   (a) from about 25 to about 150 IU/l of said lipase from *Staphylococcus epidermidis* NRRL B-12072;
   (b) from about 300 to about 1500 IU/l glycerol kinase;
   (c) from about 0.5 to about 3 mM adenosine triphosphate;
   (d) from about 0.2 to about 2 mM of a co-enzyme selected from a group consisting of NAD, NADP, derivatives thereof, and mixtures thereof;
   (e) from about 2 to about 30 mM $Mg^{++}$;
   (f) from about 4,000 to about 25,000 IU/l glycerol phosphate dehydrogenase;
   (g) from about 2,000 to about 20,000 IU/l diaphorase; and
   (h) from about 0.1 to about 0.25 g/l 2-(p-indophenyl)-3-p-nitrophenyl-5-phenyl-tetrazolium chloride.

10. The kit of claims 1–5 or 6 having a pH of about 7 to about 8 and comprising:
    (a) from about 50 to about 100 IU/l of said lipase from *Staphylococcus epidermidis* NRRL B-12072;
    (b) from about 600 to about 1,200 IU/l glycerol kinase;
    (c) from about 1 to about 2 mM adenosine triphosphate;
    (d) from about 0.5 to about 1 mM of a co-enzyme selected from a group consisting of NAD, NADP, derivatives thereof and mixtures thereof;
    (e) from about 10 to about 20 mM $Mg^{++}$;
    (f) from about 10,000 to about 15,000 IU/l glycerol phosphate dehydrogenase;
    (g) from about 5,000 to about 15,000 IU/l diaphorase; and
    (h) from about 0.12 to about 0.2 gm/l 2-(p-indophenyl)-3-p-nitrophenyl-5-phenyl-tetrazolium chloride.

11. The kit of claims 1–5 or 6 having a pH of about 7.5±0.1 and comprising:
    (a) about 75 IU/l of said lipase from *Staphylococcus epidermidis* NRRL B-12072;
    (b) about 920 IU/l of said glycerol kinase;
    (c) about 1.32 mM adenosine triphosphate;
    (d) about 0.68 mM of a co-enzyme selected from a group consisting of NAD, NADP, derivatives thereof, and mixtures thereof;
    (e) about 16.78 mM $Mg^{++}$;
    (f) about 15,000 IU/l of glycerol phosphate dehydrogenase;
    (g) about 10,000 IU/l of diaphorase; and
    (h) about 0.187 gm/l of 2-(p-indophenyl)-3-p-nitrophenyl-5-phenyl-tetrazolium chloride.

12. The kit of claims 1–5 or 6 wherein said reagent is capable of being used to assay adenosine diphosphate and comprises a reduced co-enzyme selected from a group consisting of NADH, NADPH, derivatives thereof, and mixtures thereof, phosphoenol pyruvate, $Mg^{++}$, pyruvate kinase, and lactate dehydrogenase.

13. The kit of claims 1–5 or 6 having a pH of from about 6 to about 8 and comprising:
    (a) at least about 20 IU/l of said lipase from *Staphylococcus epidermidis* NRRL B-12072;
    (b) at least about 100 IU/l glycerol kinase;
    (c) at least about 0.1 mM adenosine triphosphate;
    (d) at least about 0.2 mM of a reduced co-enzyme selected from a group consisting of NADH, NADPH, mixtures thereof, and derivatives thereof;
    (e) at least about 1 mM $Mg^{++}$;
    (f) at least about 0.1 mM phosphoenol pyruvate;
    (g) at least about 300 IU/l pyruvate kinase; and
    (h) at least about 300 IU/l lactate dehydrogenase.

14. The kit of claims 1–5 or 6 having a pH of from about 6 to about 8 and comprising:
    (a) from about 20 to about 150 IU/l of said lipase from *Staphylococcus epidermidis* NRRL B-12072;
    (b) from about 1,000 to about 2,500 IU/l glycerol kinase;
    (c) from about 0.1 to about 0.8 mM adenosine triphosphate;
    (d) from about 0.2 to about 0.6 mM of a reduced co-enzyme selected from a group consisting of NADH, NADPH, derivatives thereof, and mixtures thereof;
    (e) from about 1 to about 10 mM $Mg^{++}$;
    (f) from about 0.1 to about 0.8 mM phosphoenol pyruvate;
    (g) from about 300 to about 6000 IU/l pyruvate kinase; and
    (h) from about 300 to about 2,000 IU/l lactate dehydrogenase.

15. The kit of claims 1–5 or 6 having a pH of from about 6.5 to about 7.5 and comprising:
    (a) from about 30 to about 75 IU/l of said lipase from *Staphylococcus epidermidis* NRRL B-12072;
    (b) from about 2,000 to about 3,000 IU/l glycerol kinase;
    (c) from about 3 to about 8 mM adenosine triphosphate;
    (d) from about 0.25 to about 0.35 of a reduced co-enzyme selected from a group consisting of NADH, NADPH, derivatives thereof, and mixtures thereof;
    (e) from about 3 to about 8 mM $Mg^{++}$;
    (f) from about 0.2 to about 0.6 mM phosphoenol pyruvate;
    (g) from about 2,500 to about 3,500 IU/l pyruvate kinase; and
    (h) from about 1,000 to about 1,800 IU/L lactate dehydrogenase.

16. The kit of claims 1–5 or 6 having a pH of about 7.1±0.1 and comprising:
    (a) about 50 IU/l of said lipase from *Staphylococcus epidermidis* NRRL B-12072;
    (b) about 2,500 IU/l glycerol kinase;
    (c) about 0.3 mM adenosine triphosphate;

(d) about 0.3 mM of a reduced co-enzyme selected from a group consisting of NADH, NADPH, derivatives thereof, and mixtures thereof;
(e) about 5 mM $Mg^{++}$;
(f) about 0.37 mM phosphoenol pyruvate;
(g) about 2,990 IU/l pyruvate kinase; and
(h) about 1,485 IU/l lactate dehydrogenase.

17. An assay of endogenous glycerol and triglycerides in a sample to be assayed comprising:
(a) performing reactions which comprise:
(i) reacting said endogenous glycerol with adenosine triphosphate in the presence of glycerol kinase to form glycerol-1-phosphate and adenosine diphosphate;
(ii) determining the amount of endogenous glycerol by measuring the amount of one of said reaction products of step (i);
(iii) adding to said reaction medium a surfactant capable of activating a lipase from *Staphylococcus epidermidis* NRRL B-12072 said lipase being added to said reaction medium prior to the addition of said surfactant thereto;
(iv) reacting triglycerides in the presence of said activated lipase to form glycerol and free fatty acids;
(v) reacting said glycerol formed in step (iv) with adenosine triphosphate in the presence of glycerol kinase to form glycerol-1-phosphate and adenosine;
(vi) determining the amount of triglyceride by measuring the amount of one of said reaction products of step (v).

18. The assay of claim 17 wherein:
(a) said glycerol-1-phosphate formed in step (i) is reacted with a co-enzyme selected from a group consisting of NAD, NADP, derivatives thereof, and mixtures thereof in the presence of glycerol phosphate dehydrogenase to form dihydroxyacetone phosphate and the reduced form of said co-enzyme;
(b) said reduced form of said co-enzyme formed in step (a) is reacted with 2-(p-indophenyl)-3-p-nitrophenyl-5-phenyl-tetrazolium chloride in the presence of diaphorase to form formazan and said co-enzyme; and
(c) the formation of said formazan formed in step (b) is spectrophotometrically measured;
(d) said glycerol-1-phosphate formed in step (v) is reacted with a co-enzyme selected from a group consisting of NAD, NADP, derivatives thereof, and mixtures thereof in the presence of glycerol phosphate dehydrogenase to form dihydroxyacetone phosphate and the reduced form of said co-enzyme;
(e) said reduced form of said co-enzyme formed in step (d) is reacted with 2-(p-indophenyl)-3-p-nitrophenyl-5-phenyl-tetrazolium chloride in the presence of diaphorase to form formazan and said co-enzyme; and
(f) the formation of said formazan formed in step (e) is spectrophotometrically measured.

19. The assay of claim 17 wherein:
(a) said adenosine diphosphate formed in step (i) is reacted with phosphoenol pyruvate in the presence of pyruvate kinase to form adenosine triphosphate and pyruvate;
(b) said pyruvate formed in step (a) is reacted with a reduced co-enzyme selected from a group consisting of NADH, NADPH, derivatives thereof, and mixtures thereof in the presence of lactate dehydrogenase to form lactate and the oxidized form of said co-enzyme;
(c) the production of said oxidized co-enzyme formed in step (b) is measured;
(d) said adenosine diphosphate formed in step (iv) is reacted with phosphoenol pyruvate in the presence of pyruvate kinase to form adenosine triphosphate and pyruvate;
(e) said pyruvate formed in step (d) is reacted with a reduced co-enzyme selected from a group consisting of NADH, NADPH, derivatives thereof, and mixtures thereof in the presence of lactate dehydrogenase to form lactate and the oxidized form of said co-enzyme;
(f) the production of said oxidized co-enzyme formed in step (e) is measured.

* * * * *